(12) United States Patent
Anderson et al.

(10) Patent No.: US 8,449,836 B2
(45) Date of Patent: May 28, 2013

(54) FIXTURES FOR USE IN PARALLEL PROCESSING BIO-CHIPS

(75) Inventors: Clifford L. Anderson, Tempe, AZ (US); Richard E. Maldonado, Fountain Hills, AZ (US); Richard D. Belval, Jr., New Fairfield, CT (US)

(73) Assignee: GE Healthcare Bio-Sciences AB, Uppsala (SE)

( * ) Notice: Subject to any disclaimer, the term of this patent is extended or adjusted under 35 U.S.C. 154(b) by 103 days.

(21) Appl. No.: 12/469,714

(22) Filed: May 21, 2009

(65) Prior Publication Data

US 2010/0040507 A1   Feb. 18, 2010

Related U.S. Application Data

(63) Continuation of application No. 10/486,932, filed as application No. PCT/US02/26078 on Aug. 16, 2002, now abandoned, application No. 12/469,714, which is a continuation of application No. 10/216,057, filed on Aug. 9, 2002, now abandoned.

(60) Provisional application No. 60/312,719, filed on Aug. 16, 2001.

(51) Int. Cl.
    *B01L 3/00*      (2006.01)
(52) U.S. Cl.
    USPC ............ 422/500; 422/62; 422/501; 422/502; 422/503; 422/504; 436/43; 436/46
(58) Field of Classification Search
    USPC ............ 422/61, 99, 101, 102, 104, 300, 430, 422/547, 551, 552, 560, 561, 563, 62, 500–504; 206/45.2, 223, 438, 456, 557, 561, 562, 564, 206/565, 751, 752; 436/43, 46; 211/40, 41.11, 211/41.13, 41.14; 248/312.1, 451, 452, 488, 248/490; 220/526, 529, 532
    See application file for complete search history.

(56) References Cited

U.S. PATENT DOCUMENTS

| | | | |
|---|---|---|---|
| 2,119,407 A | | 5/1938 | Weiskopf |
| 3,244,273 A | * | 4/1966 | Wiklund ................. 206/456 |
| 4,735,778 A | | 4/1988 | Maruyama et al. |
| 4,801,431 A | * | 1/1989 | Cuomo et al. ............. 422/563 |
| 4,960,224 A | * | 10/1990 | Boenisch ................. 206/456 |
| 5,023,187 A | | 6/1991 | Koebler et al. |
| 5,653,942 A | | 8/1997 | Terashima et al. |
| 5,869,006 A | | 2/1999 | Fanning et al. |
| 5,897,835 A | | 4/1999 | Seaton et al. |
| 5,955,373 A | | 9/1999 | Hutchins et al. |
| 6,004,512 A | | 12/1999 | Titcomb et al. |
| 6,017,495 A | | 1/2000 | Ljungmann |

(Continued)

FOREIGN PATENT DOCUMENTS

DE   9401303    4/1994

*Primary Examiner* — Jyoti Nagpaul

(57) ABSTRACT

A holder (10) housing defines a plurality of individual wells (14) sized to retain a substrates such as a bio-chip (20) or microscope slide in a vertical orientation, and to retain a volume of liquid (22) sufficient to immerse the bio-chip. The wells are spaced-apart with an approximately 9 mm pitch and the holder has a form factor approximating an SBS Standard 96-well microplate. The holder configuration is such that it can be manipulated with standard robotic equipment (30), and can be fabricated using injection molding processes.

11 Claims, 5 Drawing Sheets

U.S. PATENT DOCUMENTS

| | | |
|---|---|---|
| 6,635,225 B1 | 10/2003 | Thiem et al. |
| 2002/0150450 A1 | 10/2002 | Bevirt et al. |
| 2003/0111373 A1* | 6/2003 | Chouinard et al. ........... 206/456 |
| 2003/0175170 A1* | 9/2003 | Youngquist et al. .......... 422/104 |

* cited by examiner

FIXTURES FOR USE IN PARALLEL PROCESSING BIO-CHIPS

PRIORITY CLAIM

This application is a continuation of U.S. patent application Ser. No. 10/486,932, filed Jan. 6, 2005, abandoned, which is a filing under 35 U.S.C. §371 and claims priority to international patent application number PCT/US02/26078 filed Aug. 16, 2002, published on Feb. 27, 2003 as WO 03/015921, which claims priority to U.S. patent application Nos. 60/312,719 filed Aug. 16, 2001 and this application is a continuation of U.S. patent application Ser. No. 10/216,057 filed Aug. 9, 2002 now abandoned.

FIELD OF THE INVENTION

The invention relates generally to fixtures that hold bio-chips, microscope slides and the like, and more particularly to fixtures that can be manipulated either manually or robotically during parallel processing of bio-chips, including bio-chips in microscope-slide format.

BACKGROUND OF THE INVENTION

A variety of bio-chips is known in the art. Typically a bio-chip includes a substrate upon which an array of test sites may be defined, the number of sites ranging from a thousand to ten thousand or more on a bio-chip that measures perhaps a few cm by a few cm. Various experiments may be carried out at the various sites, e.g., using reagents, and frequently the bio-chip will be moved, manually or robotically during experiments or testing.

Robotic repositioning of bio-chips is preferred in that such manipulation is generally more accurate than manual repositioning, and can be carried out more rapidly. Understandably more rapid manipulation of bio-chips is desired in that more experiments can be carried out per unit time.

Although several prior art holders can retain multiple bio-chips, such holders frequently have shortcomings. For example, Marsh Bio Products, Inc. of Rochester, N.Y. 14610 produces the so-called DR1205 reservoir. This holder provides channels for twelve slides but requires a relatively high volume, 5 ml, of reagent per channel. Since cost of reagents can be high in various experiments, it is desired to reduce the amount of reagent needed per retained bio-chip. Other manufacturers provide holders to retain bio-chips, which holders are fabricated from expensive material, for example stainless steel. Too often, prior art bio-chip holders fail to fully protect the active surface of the bio-chip. Understandably, failing to adequately protect the bio-chip can affect the nature and quality of the test results. Various prior art bio-chip holders are configured such that robotic manipulations including microtiter formatting, automatic filling/draining of channels, automatic stacking of holders cannot readily be accomplished. Further, various prior art bio-chip holders do not provide an independent channel for each retained bio-chip, which omission can result in cross-contamination.

As such, there is a need for a fixture that can retain one or more bio-chips during various phases of experimentation, which fixture permits robotic movement such that parallel processing of bio-chips retained therein can be carried out. Further, such fixture preferably should provide an independent channel or well for retained bio-chips to minimize cross-contamination, and preferably should require a relatively small amount of reagent per bio-chip. Such holder should provide a mechanism by which each well may rapidly be filled or emptied with a liquid of interest. Such fixture preferably should be made of a relatively inexpensive material, and should robustly protect bio-chips retained therein.

The present invention provides such a fixture, and a method of retaining bio-chips while permitting manual and/or robotic manipulation of the bio-chips. Further the present invention can accommodate standard glass microscope slides as well and can facilitate manual and/or robotic manipulation of such slides for a variety of applications.

SUMMARY OF THE INVENTION

A holder according to the present invention includes a housing that defines a plurality of individual wells or channels for retaining a liquid and a bio-chip intended to react in some manner with the liquid. The holder and each well is sized to retain a relatively minimal amount of liquid, while ensuring that a bio-chip inserted into the well is fully immersed. Inter-well fluid-communication does not occur and resultant cross-contamination is thus reduced. The holder configuration is preferably standardized in size and form factor such that conventional microscope slide-sized bio-chips are retained, and the holder itself may be manipulated with standard robotic mechanisms. Further, the holder is sized to be sealingly covered with standard lids, or with tools according to the present invention. The various holders and tools preferably are configured to be fabricated from durable material, using standardized techniques such as injection molding. Tools and reservoirs for use with an array of bio-chips are also described. The holders may also receive standard microscope slides, enabling the present invention to be used in applications including slide staining, e.g., for histology, cytology, etc.

Other features and advantages of the invention will appear from the following description in which the preferred embodiments have been set forth in detail, in conjunction with the accompanying drawings.

DETAILED DESCRIPTION OF THE PREFERRED EMBODIMENT

The present invention provides a variety of holders and tools for the manipulation of a plurality of bio-chips for hybridization, washing and analysis steps. In particular, the holders and tools of the invention find use in assays utilizing bio-chips such as those described in PCT US 00/34145 and PCT US01/02664, both of which are expressly incorporated by reference in their entirety. These bio-chips comprise a rigid support with a flexible membrane top that encompasses the reaction chamber comprising the array of capture biomolecules, particularly nucleic acids. The chips comprise ports for the introduction of samples comprising the analytes of interest. After introduction of the sample, the bio-chips are incubated for a period of time sufficient to allow binding (referred to as hybridization when the target analyte and capture probes are nucleic acids), frequently with mixing. Washing solutions can be added with further incubation, although as described herein, the washing steps may occur later. The flexible membrane is generally removed, and then further optional washing steps can be done, followed by detection of the target analytes, usually by insertion of the bio-chips into a scanner or reader.

Accordingly, there is a need for holders and tools to allow the simultaneous manipulation of a plurality of bio-chips to reduce time, cost, labor and increase reproducibility and accuracy.

Figure 6:
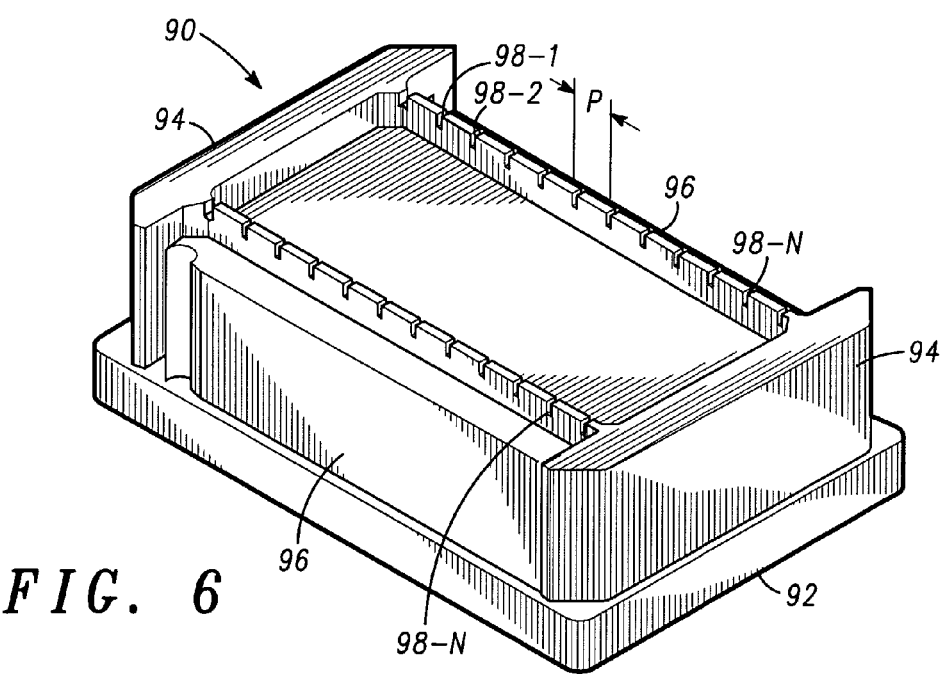
FIG. 6 is a perspective plan view of a tool for removing an array of bio-chips from a holder, according to the present invention.

Thus, the present invention provides a number of holders and tools to facilitate this manipulation. As described below, in one embodiment, the holder comprises slots into which the bio-chips are inserted, with an optional top. This holder is then inserted into a reservoir system (e.g. a two component system), that can include either a single large reservoir, such that the bio-chips are in fluid communication, or separate reservoirs, such that the bio-chips are fluidically isolated. Alternatively, the holder can comprise both slots for the insertion of the chips, as well as the reservoir (e.g. a one component system). In addition, tools are provided that allow ease of handling; for example, in a two component system, a removal tool (as depicted in FIG. 6) can be used to "pop" out the chips for transfer to other systems such as a detection system.

Figure 1:
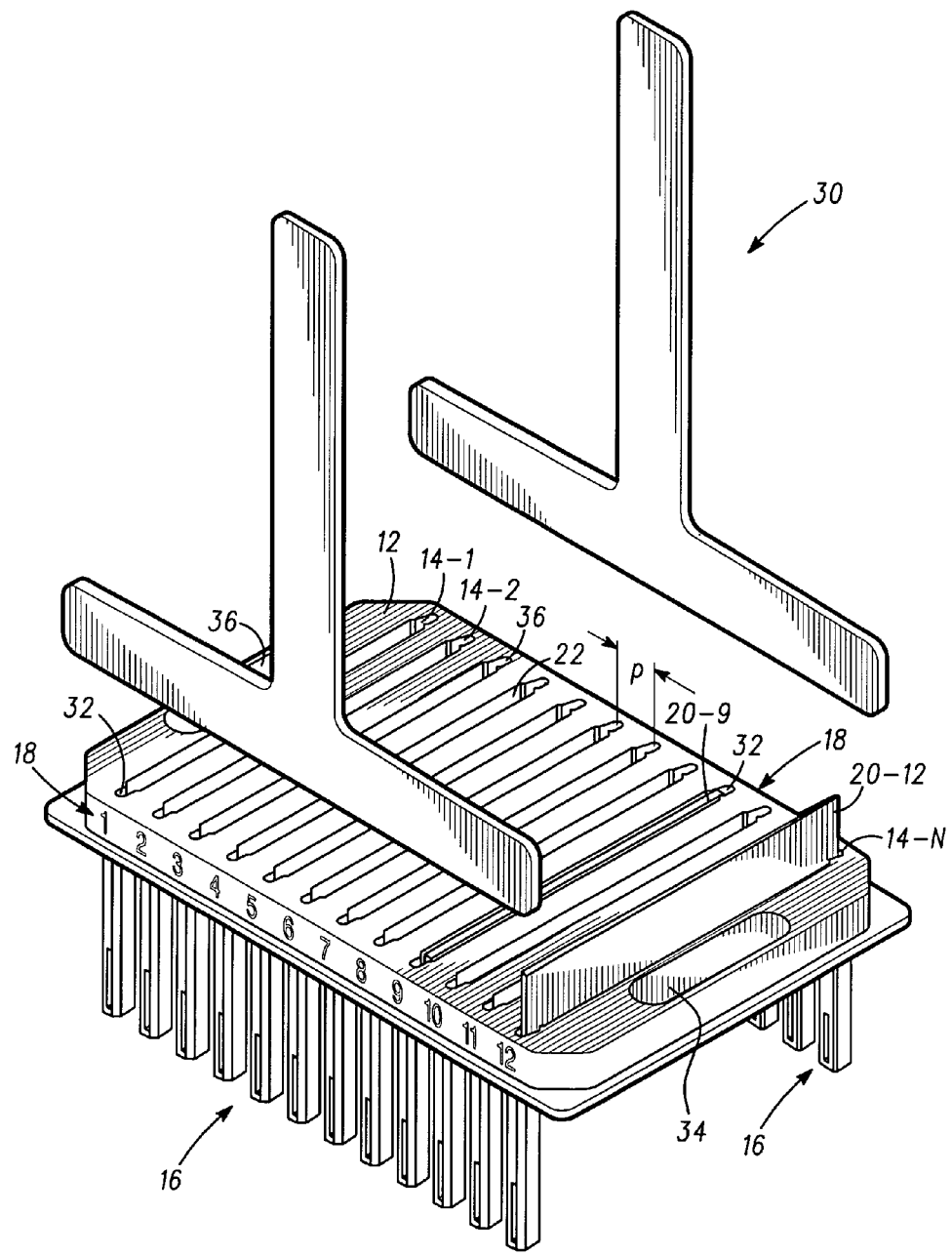
FIG. 1 is a perspective plan view of a first embodiment of a holder or bio-array rack for bio-chips, according to the present invention. This is generally described herein as a holder that is part of a two component system.

FIG. 1 depicts a first embodiment of a bio-chip holder or bio-array rack 10 comprising a housing surface 12 in which a plurality of bio-chip retaining channels or reservoirs 14 are formed. Preferably first and second sidewalls 16 are affixed to surface 12, and include indicia 18 uniquely identifying each channel. For example in FIG. 1, holder 12 provides twelve channels, for which indicia 18 includes numerals 1, 2, ... 12. The use of indicia 18 can reduce human error when dealing with bio-chips 20 inserted into or removed from a given channel. In FIG. 1, bio-chip 20-12 is shown somewhat removed from underlying channel number 12. By contrast, channel number 9 is shown with a bio-chip 20-9 substantially within the channel. One or more reagents 22 may be present in each channel 14-$x$, such that sites on a bio-chip 20-$x$ within a channel will be exposed to such reagents. Preferably channels defined in holder 10 permit completely immersing a bio-chip with reagent 22 within the channel. In the preferred embodiments described herein, each channel 14-$x$ is sized to receive a standard 1" (2.54 cm)×3" (7.62 cm)×0.04" (1.3 mm) microscope slide, which is to say, each bio-chip 20-$x$ preferably is the size of a standard microscope slide. Thus, components 20-$x$ could, if desired, be microscope slides. It is understood that holder 10 could of course include channels of varying size and volume and configuration. In a preferred embodiment, the volume of liquid used within each well for an associated bio-chip can be as little as about 3.4 ml. As noted since many reagents are costly, the ability to perform tests with a reduced volume of liquid can be very advantageous.

Preferably the outer dimensions and form factor of holder 10, and indeed each holder or tool or reservoir embodiment described herein, is such that the holders conform substantially closely to SBS Standard 96-well microplate dimensions. Such standardization of the form factor of holders according to the present invention permits existing robotic-type mechanisms, depicted generically by arm 30, to manipulate the holders and bio-chips (or microscope slides) within. (See also FIG. 7.) Further, it is preferred that the spaced-apart pitch P between adjacent channels or wells 14-$x$ in holder 10 is a standard dimension, for example a 9 mm pitch corresponding to multiple-pipet dispensing port pitches. The ability of each holder 10 to be accurately and rapidly manipulated by mechanism 30 permits holding and moving a plurality of retained bio-chips, for example from one reagent reservoir to another reservoir. In the configuration shown in FIG. 1, gravity advantageously assists in the process of loading each bio-chip 20-$x$ into a corresponding well or channel 14-$x$ in holder 10. Further, vertical grooves 32 defined in the vertical edges of each channel help retain an associated bio-chip such that the vertical surfaces (in FIG. 1) of the bio-chip do not contact the vertical walls of the well within housing 10. Further, the well configuration preferably is symmetrical such that a bio-chip can be inserted without regard to orientation, while ensuring full immersion of the relevant bio-chip surfaces in reagent or other liquid 22.

Automation using the present invention is further promoted by providing holder 10 with at least one input port 32 and at least one output port 34. Input port 32 is preferably in one-way fluid communication with each channel or well 14-$x$ in the holder, and facilitates rapidly filling each well with a liquid. Each well advantageously has a level marker 36 such that the correct fill level can be rapidly and visually confirmed. Using simple valves or the like, fluid communication is one-way such that liquid contents of one well do not communicate with the liquid contents of another well. Output port 34 can be used to rapidly purge liquid from each of the wells. Further, the form factor of each holder according to the present invention permits the holders to be stacked, and to be sealingly covered using a standard microplate lid.

Holder 10 may be fabricated in a variety of ways using any of several materials. However in a preferred embodiment, holder 10 is injection moldable to reduce manufacturing costs. Holder 10 preferably is fabricated from a material that is resistant to chemicals, for example, an acetyl copolymer material. Such material advantageously can tolerate a wide temperature range and can be easily cleaned, and in fact is dishwasher safe. Further, such material (or other material) from which holder 10 is fabricated preferably will be substantially opaque to optical energy encountered during light-sensitive testing or experimental phases of the bio-chips retained within.

Figure 2:
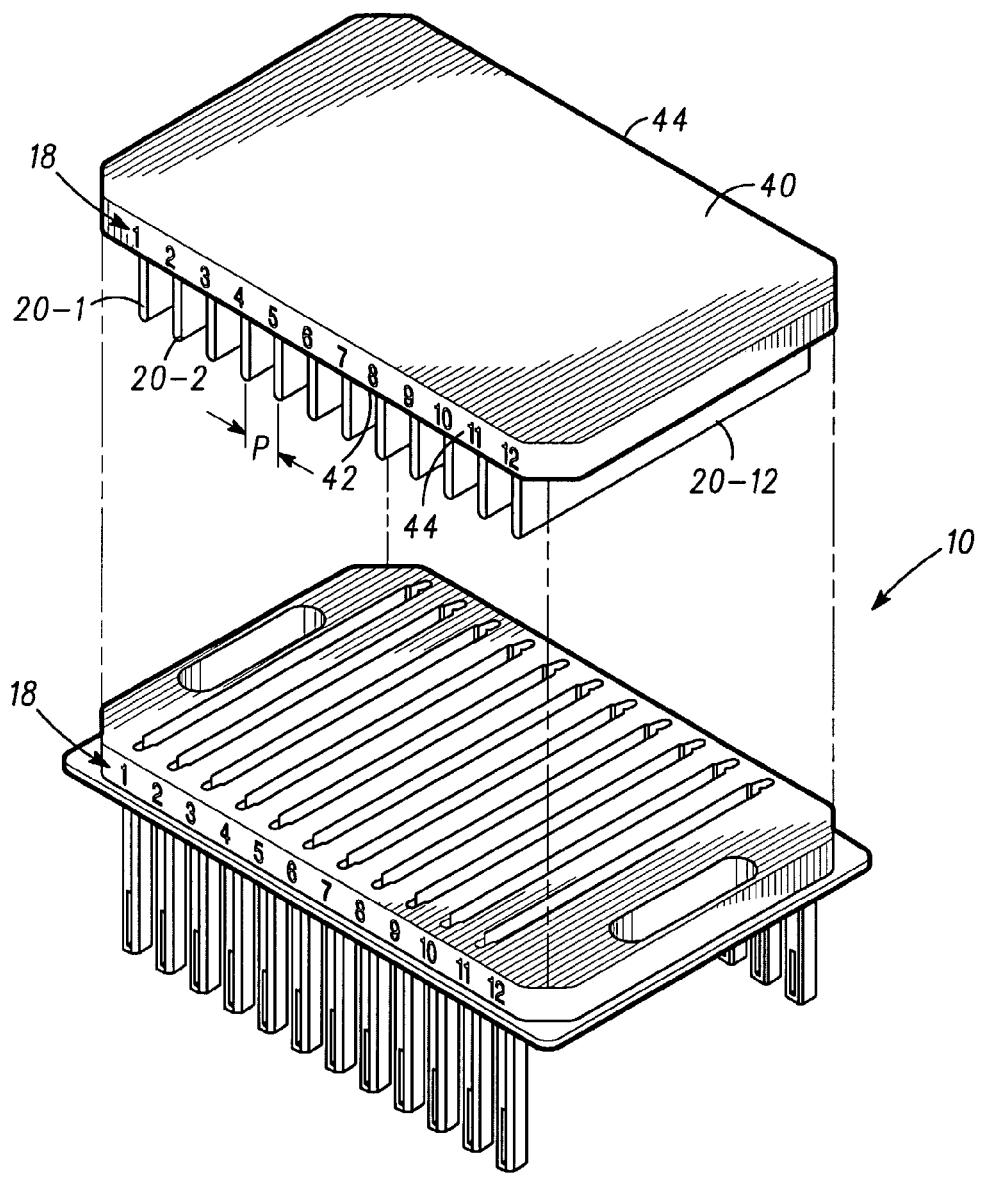
FIG. 2 is a perspective plan view of a preferred embodiment of a bio-array tool and a holder, loadable with bio-chips using the bio-array tool, according to the present invention.

FIG. 2 depicts a preferred embodiment of a bio-array positioning tool 40 that is sized to retain a plurality of bio-chips 20-$x$ with pitch P to permit tool 40 to be lowered over the upper surface of a holder, e.g. holder 10 such that each bio-chip is lowered into an associated well or channel 14 in holder 10 and is fully seated therein. (Unless otherwise noted, like reference numerals in one figure herein may be understood to refer to similar or identical elements.) The lower surface 42 of tool 40 preferably includes a mechanism 44 for retaining each bio-chip 20-$x$ within the tool. Without limitation, mechanism 44 may include a groove formed in lower surface 44 to frictionally retain an edge of each bio-chip to be held by tool 40. Use of tool 40 can advantageously promote proper seating of bio-chips 20-$x$ in holder 10 such that full immersion with reagent or other liquid 22 results. Further, tool 40 is convenient for at least partially removing the array of bio-chips from holder 10. Tool 40 preferably is fabricated using techniques and materials similar to what has been described above with respect to holder 10. As tool 40 and holder 10 preferably are uniformly sized, tool 40 can be used as a sealing lid to cover the upper surface of holder 10, with reagent and bio-chips within the holder. In a closed disposition, tool 40 preferably matingly seals to the holder 10 such that a robotic mechanism, e.g., mechanism 30 in FIG. 1, can manipulate holder 10, tool 40, and the bio-chips within.

FIG. 3 depicts what may be termed a reservoir holder 50 that defines a plurality of individual channels or wells 14-1, 14-2, . . . 14-N, each sized to retain a liquid or reagent 22 and to receive a bio-chip such as bio-chip 20-x, described above with reference to FIGS. 2 and 3. Holder 50 includes four sides 52, a bottom 54, and a top member 56 that defines individual wells or channels 14-x. Again, it is understood that holder 50 is sized such that it may be sealingly covered with a standard lid including tool 40. If desired, each channel or well 14-x formed in upper member 56 may include an enlarged end region 58 to promote more rapid filling with liquid or reagent 22. It is understood that in the preferred embodiment there is no cross-contamination from fluid in one channel with fluid in another channel in holder 50.

Figure 3:
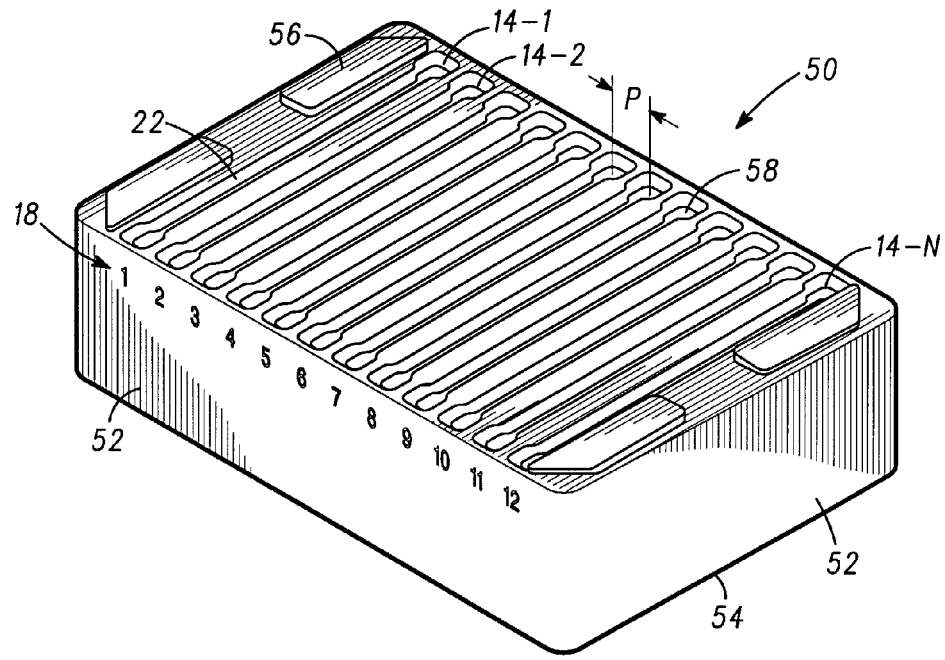
FIG. 3 is a perspective plan view of an embodiment of a reagent reservoir holder for receiving bio-chips, according to the present invention. This is part of a two component system.
Figure 4:
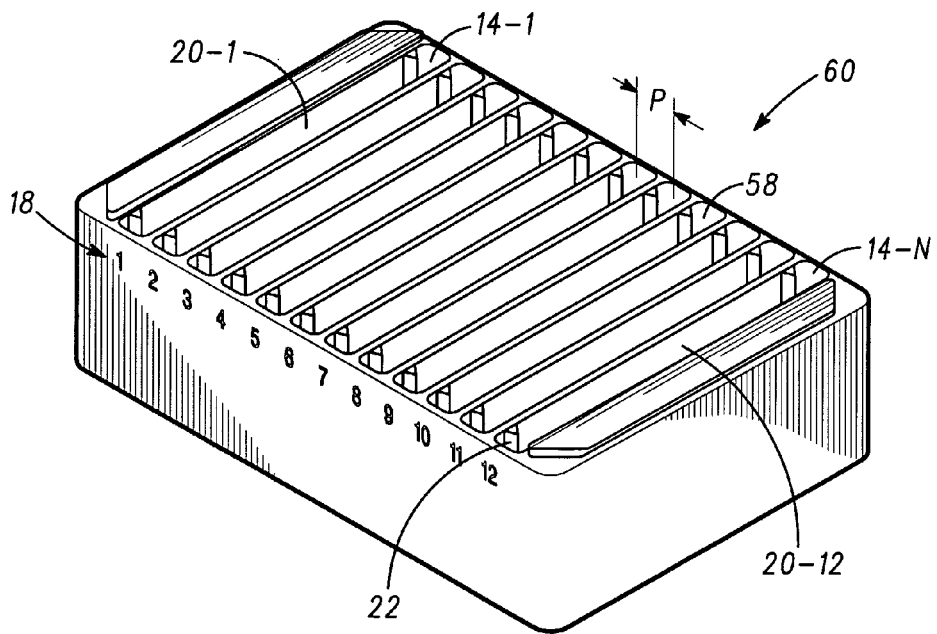
FIG. 4 is a perspective plan view of an alternative embodiment of a reagent reservoir holder for receiving bio-chips, according to the present invention.
Figure 5:
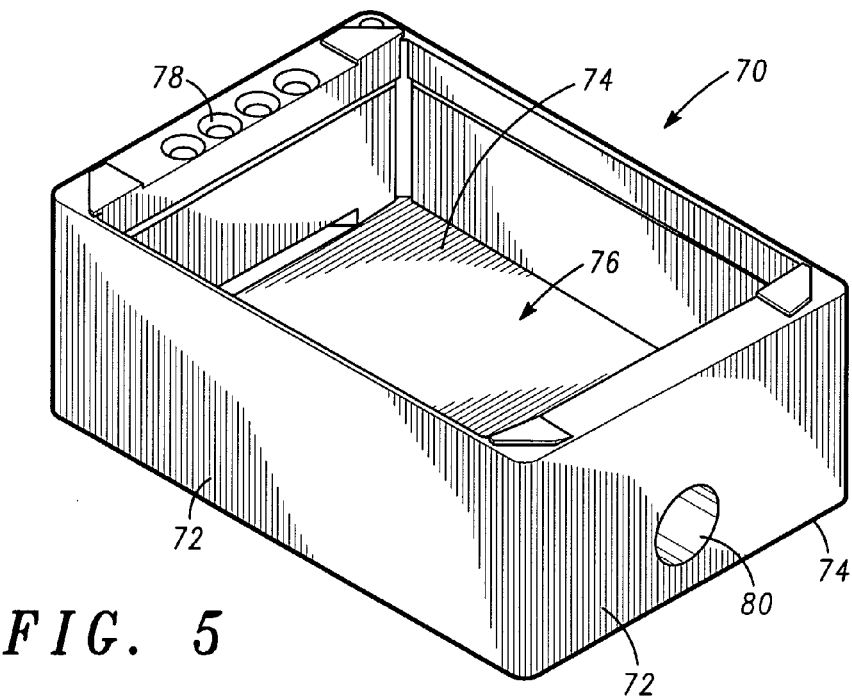
FIG. 5 is a perspective plan view of a fifth embodiment of a holder for bio-chips, according to the present invention.

FIG. 4 depicts a reservoir holder 60 similar to holder 50 shown in FIG. 3, except that optionally a larger volume of reagent 22 may be retained within. FIG. 5 depicts an embodiment of a reservoir holder 70 that preferably retains more liquid or reagent 22 than does holder 60 or holder 50. Reservoir holder 70 comprises four side walls 72, and bottom member 74 and defines an open volume 76 within that may be filled with liquid or reagent 22. Once filled with a liquid, tool 40 (or the like) loaded with bio-chips 20-x may be lowered over holder 70 such that each bio-chip is immersed in the liquid retained within volume 76. Holder 70 preferably includes at least one input port 78 and at least one output port 80 to facilitate the rapid filling and draining of volume 76 with liquid 22. Port 80 may be used, for example, as a bleed opening in a water bath phase of parallel-processing of bio-chips. Again, it is understood that holder 70 like the other holders described herein is sized such that a standard lid including tool 40 may be sealing attached to the top portion of the holder. Further, the standardized form factor of the various holders described herein is such that holder 70 may be manipulated with a robotic mechanism such as mechanism 30 (see FIG. 1).

Turning now to FIG. 6, a bio-array removal tool 90 is depicted. Removal tool 90 includes a base member 92, two spaced-apart short sidewall members 9 and two spaced-apart longer sidewall members 96. An upper ledge formed on each of the long sidewall members 96 defines a series of notches 98-x, preferably spaced-apart with the same pitch P as was defined with regard to FIGS. 1-4. Notches 98-x in removal tool 90 can frictional engage respective edges of bio-chips 20-x for purposes of at least partially withdrawing the bio-chips from a holder, for example holder 10 in FIG. 1. It is understood that preferably removal tool 90 may be fabricated using techniques and materials similar to that used for the various embodiments of tools and holders described above herein.

Figure 7:
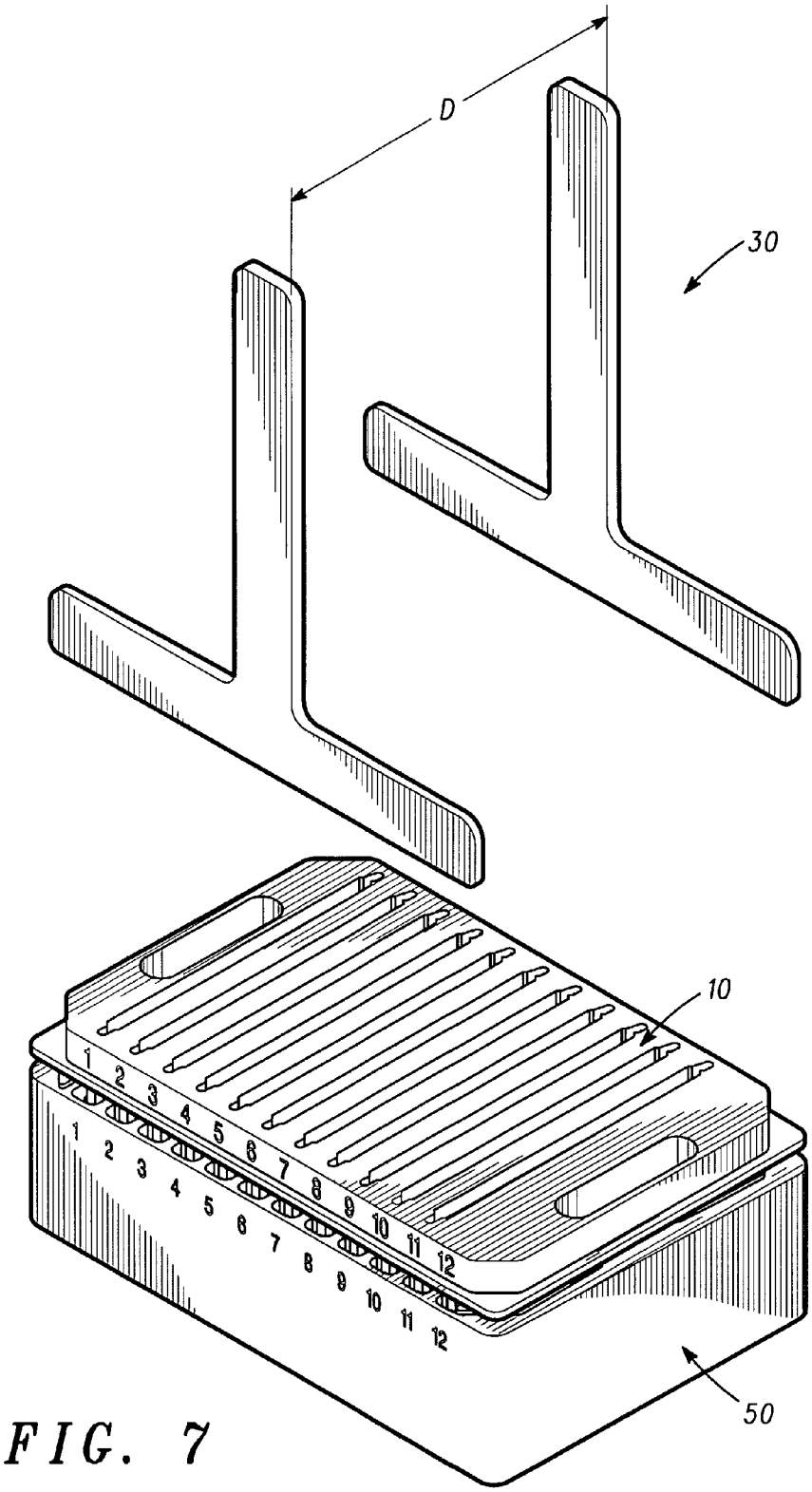
FIG. 7 is a perspective plan view showing a bio-chip holder and reagent reservoir, according to the present invention, and a robotic mechanism.

FIG. 7 shows a robotic mechanism 7 in juxtaposition over a reservoir such as reservoir 50 described with respect to FIG. 3, and an overlying holder such as holder 10 described with respect to FIG. 1. Preferably the spaced-apart distance D between arms of the robotic mechanism is such that the mechanism can fit within the preferably about 1.5 mm or about 3 mm gap clearance provided on either side of holder 10 and reservoir 50. This gap clearance helps minimize capillary action that could cause fluid to cross between channels, such as channels 14-x, described earlier herein. The modular-like design of the present invention is such that when positioning tool 40 (see FIG. 2) is inserted into a holder, e.g., 10, robotic mechanism 30 can be controlled to selectively manipulate, e.g., pick-up, only positioning tool 40, or positioning tool 40 and holder 10, or to pick-up positioning tool 40, holder 10, and reservoir 50.

In summary, the various embodiments of the present invention provide holders or fixtures, reservoirs, and tools that can expedite the parallel processing of bio-chips. In contrast to prior art mechanisms, the described embodiments lend themselves to robotic manipulation and are useable with standardized components such as lids, and microscope slide-sized bio-chips. While exemplary dimensions and form factors have been described, it is understood that other dimensions and shapes could instead be used.

In addition, as will also be appreciated by those in the art, the holders, tools and biochips of the invention may be part of high throughput screening (HTS) system utilizing any number of components. Fully robotic or microfluidic systems include automated liquid-, particle-, cell- and organism-handling including high throughput pipetting to perform all steps of gene targeting and recombination applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

The system used can include a computer workstation comprising a microprocessor programmed to manipulate a device selected from the group consisting of a thermocycler, a multichannel pipettor, a sample handler, a plate handler, a gel loading system, an automated transformation system, a gene sequencer, a colony picker, a bead picker, a cell sorter, an incubator, a light microscope, a fluorescence microscope, a spectrofluorimeter, a spectrophotometer, a luminometer, a CCD camera and combinations thereof.

It is also to be understood that the present invention may be used in various manipulation of microscope slide-sized slides aside from bio-chips. Without limitation, exemplary other such uses could include ctyology staining, parasite staining, and various cell culture techniques.

Modifications and variations may be made to the disclosed embodiments without departing from the subject and spirit of the invention as defined by the following claims.

What is claimed is:

1. A kit for use with a plurality of substrates selected from a group consisting of bio-chips and microscope slides, comprising:
   a holder including a housing whose upper region defines a plurality of separate channels spaced-apart from each other with a pitch P, each of said channels sized to receive one of said substrates in a vertical orientation and to retain an amount of liquid sufficient to immerse a received substrate;
   a reservoir holder sized to receive said holder;
   a positioning tool sized to retain the plurality of said substrates spaced-apart from each other with said pitch P; and a removal tool for removing said plurality of substrates from said holder, said removal tool comprises: a base member; two spaced-apart short sidewall members; and two spaced-apart longer sidewall members, wherein an upper ledge formed on each of said longer sidewall members defines a series of notches, spaced-apart with the same pitch P of said holder; said notches can frictionally engage respective edges of substrates in said holder to at least partially withdrawing said substrates from said holder.

2. The kit of claim 1, wherein an upper surface of holder conforms to an SBS Standard 96-well microplate.

3. The kit of claim 1, wherein said pitch P is about 9 mm.

4. The kit of claim 1, wherein each of said substrates is a bio-chip having the same dimensions as a standard microscope slide.

5. The kit of claim 1, further including a lid member, with dimensions sized to sealingly attach to an upper surface of said holder.

6. The kit of claim 1, wherein volume of liquid retainable in each said channel is less than about 4 ml.

7. The kit of claim 1, wherein volume of liquid retainable in each said channel is about 3.4 ml.

8. The kit of claim 1, wherein said holder is manufactured by an injection molding technique.

9. The kit of claim 1, wherein each of said holder, said reservoir holder and said positioning tool is sized to accommodate manipulation by a robotic mechanism.

10. The kit of claim 1, wherein said reservoir holder is a single large reservoir holder.

11. The kit of claim 1, wherein said reservoir holder consists of separate reservoirs such that each substrate is fluidically isolated in use.

* * * * *